(12) United States Patent
Nakahashi

(10) Patent No.: US 9,465,117 B2
(45) Date of Patent: Oct. 11, 2016

(54) RADIATION DETECTING APPARATUS

(71) Applicant: FUJIFILM Corporation, Minato-ku, Tokyo (JP)

(72) Inventor: Hiroshi Nakahashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 45 days.

(21) Appl. No.: 14/830,775

(22) Filed: Aug. 20, 2015

(65) Prior Publication Data

US 2015/0369931 A1 Dec. 24, 2015

Related U.S. Application Data

(63) Continuation of application No. 13/441,454, filed on Apr. 6, 2012, now Pat. No. 9,140,809.

(30) Foreign Application Priority Data

Apr. 7, 2011 (JP) ................................ 2011-085292

(51) Int. Cl.
  *G01T 1/20* (2006.01)
  *A61B 6/10* (2006.01)
  *G03B 42/04* (2006.01)

(52) U.S. Cl.
  CPC ............. *G01T 1/2018* (2013.01); *A61B 6/102* (2013.01); *G03B 42/04* (2013.01)

(58) Field of Classification Search
  CPC .................................................. G01T 1/2018
  See application file for complete search history.

(56) References Cited

U.S. PATENT DOCUMENTS

| 5,940,686 A | * | 8/1999 | Vasquez | ............ H01L 23/49531 257/E23.036 |
| 7,719,845 B1 | * | 5/2010 | Jang | ................. G06K 19/07732 174/521 |
| 2002/0005490 A1 | * | 1/2002 | Watanabe | ............. G01T 1/2018 250/370.09 |
| 2007/0165785 A1 | * | 7/2007 | Watanabe | ................ A61B 6/00 378/189 |
| 2008/0118034 A1 | | 5/2008 | Aoyagi | |

(Continued)

FOREIGN PATENT DOCUMENTS

| JP | 2003185753 A | 7/2003 |
| JP | 2004296656 A | 10/2004 |

(Continued)

OTHER PUBLICATIONS

Tapson, Oxford Mathematics Study Dictionary, Jul. 1999, Oxford University Press, Second Edition, pp. 1-9.

(Continued)

*Primary Examiner* — David Porta
*Assistant Examiner* — Jeremy S Valentiner
(74) *Attorney, Agent, or Firm* — Sughrue Mion, PLLC

(57) ABSTRACT

A radiation detecting apparatus includes a radiation detector including a scintillator for converting radiation that has passed through a subject into visible light, and a substantially rectangular shaped photoelectric transducer board for converting the visible light into radiographic image information, and a casing housing the radiation detector therein. The casing is of a substantially rectangular shape and includes an upper plate, a lower plate, and a frame interconnecting the upper plate and the lower plate. The frame has a recess defined therein, which faces and is spaced from a corner of the photoelectric transducer board, the recess being concave in a direction away from the corner.

8 Claims, 11 Drawing Sheets

(56) References Cited

U.S. PATENT DOCUMENTS

| | | | |
|---|---|---|---|
| 2008/0296783 A1* | 12/2008 | Enomoto | H01L 23/3107 257/783 |
| 2009/0020873 A1* | 1/2009 | Watanabe | H01L 21/561 257/737 |
| 2009/0026379 A1 | 1/2009 | Yaegashi et al. | |
| 2009/0202038 A1* | 8/2009 | Wu | A61B 6/4283 378/62 |
| 2009/0202044 A1 | 8/2009 | Wu et al. | |
| 2009/0224235 A1 | 9/2009 | Kitamura et al. | |

FOREIGN PATENT DOCUMENTS

| | | | |
|---|---|---|---|
| JP | 2005172511 A | 6/2005 |
| JP | 2003185753 A | 7/2006 |
| JP | 2007300996 A | 11/2007 |
| JP | 2008129231 A | 6/2008 |
| JP | 200932854 A | 2/2009 |
| JP | 2009189789 A | 8/2009 |
| JP | 2009189790 A | 8/2009 |
| JP | 2009212389 A | 9/2009 |
| JP | 2009257914 A | 11/2009 |
| JP | 2009300084 A | 12/2009 |
| JP | 2010160044 A | 7/2010 |
| JP | 2010197404 A | 9/2010 |

OTHER PUBLICATIONS

Rejection of the Application, dated May 21, 2013, issued in corresponding JP Application No. 2011-085292, 7 pages in English and Japanese.

* cited by examiner

RADIATION DETECTING APPARATUS

CROSS-REFERENCE TO RELATED APPLICATION

This application is a continuation of U.S. application Ser. No. 13/441,454, filed Apr. 6, 2012, which is based upon and claims the benefit of priority from Japanese Patent Application No. 2011-085292 filed on Apr. 7, 2011, the content of each of which is incorporated herein by reference in its entirety.

BACKGROUND OF THE INVENTION

1. Field of the Invention

The present invention relates to a radiation detecting apparatus including a radiation conversion panel housed in a casing.

2. Description of the Related Art

In the medical field, there have widely been employed radiographic image capturing apparatus that apply a radiation to a subject and guide radiation that has passed through the subject to a radiation detector, which captures radiographic image information of the subject from the radiation. Known forms of radiation detectors include a conventional radiation film for recording radiographic image information by way of exposure, and a stimulable phosphor panel for storing radiation energy representing radiographic image information in a phosphor, and reproducing the radiographic image information as stimulated light by applying stimulating light to the phosphor. The radiation film with the recorded radiographic image information is supplied to a developing device to develop the radiographic image information, or alternatively, the stimulable phosphor panel is supplied to a reading device, which reads a visible image from the radiographic image information.

Radiation detecting apparatus are widely used in operating theaters of hospitals to provide surgeons with medical imaging information. In operating theaters, it is often necessary to read recorded radiographic image information from a radiation detecting apparatus immediately after such radiographic image information has been captured, for the purpose of quickly and appropriately treating the patient. To meet such a requirement, there have been developed radiation detecting apparatus, which convert radiation directly into an electric signal, or which incorporate a photoelectric transducer board for converting radiation into visible light with a scintillator and then converting the visible light into an electric signal (see, for example, Japanese Laid-Open Patent Publication No. 2009-257914, Japanese Laid-Open Patent Publication No. 2010-197404, Japanese Laid-Open Patent Publication No. 2010-160044, Japanese Laid-Open Patent Publication No. 2007-300996, and Japanese Laid-Open Patent Publication No. 2003-185753).

SUMMARY OF THE INVENTION

While the radiation detecting apparatus is carried from place to place, the radiation detecting apparatus may accidentally be dropped onto the floor or be touched or hit by another object. In the event of such an accident, at least the photoelectric transducer board tends to contact a side wall of a casing of the radiation detecting apparatus, and to have a corner thereof deformed or damaged under the overall weight of the photoelectric transducer board, if the corner is in a lowermost position when the radiation detecting apparatus is dropped onto the floor, or if the corner is located near the object when the radiation detecting apparatus is touched or hit by the object. The radiation detecting apparatus disclosed in the above publications do not incorporate structures therein for protection against risks of accidental damage.

It is an object of the present invention to provide a radiation detecting apparatus, which keeps casing side walls mechanically strong and prevents a photoelectric transducer board, e.g., corners thereof, from becoming damaged, thereby enabling increased operational reliability during use, even if the radiation detecting apparatus is accidentally dropped onto the floor or is touched or hit by another object while the radiation detecting apparatus is carried.

According to the present invention, there is provided a radiation detecting apparatus comprising a radiation detector including a scintillator for converting radiation that has passed through a subject into visible light, and a substantially cuboid shaped photoelectric transducer board for converting the visible light into radiographic image information. The radiation detecting apparatus further comprises a casing housing the radiation detector therein, wherein the casing is of a substantially cuboid shape and includes an upper plate, a lower plate, and a side plate interconnecting the upper plate and the lower plate. The side plate has a recess defined therein, which faces toward and is spaced from a corner of the photoelectric transducer board, the recess being concave in a direction away from the corner.

More specifically, the recess is defined in a corner on the inner peripheral edge of the side plate in facing relation to the corner of the photoelectric transducer board. Therefore, a sufficient mechanical strength of the side plate, which is required to connect the upper plate and the lower plate, is not lowered.

Since the recess is concave in the direction away from the corner of the photoelectric transducer board, even if the radiation detecting apparatus is dropped by mistake onto the floor or is touched or hit by another object while the radiation detecting apparatus is being carried, only the sides of the photoelectric transducer board are likely to contact the sides, i.e., the inner wall surfaces, of the side plate, whereas the corner of the photoelectric transducer board does not come into contact with or impinge on the frame. Even if some of the sides of the photoelectric transducer board are brought into contact with some of the inner wall surfaces of the side plate, the photoelectric transducer board is supported simultaneously by two of the inner wall surfaces, and hence the overall weight of the photoelectric transducer board is not concentrated on a local region of the side plate. Consequently, the photoelectric transducer board is free of risks of damage caused by the sides, i.e., the inner wall surfaces, of the side member.

According to the present invention, as described above, even if the radiation detecting apparatus is dropped by mistake onto the floor or is touched or hit by another object while the radiation detecting apparatus is being carried, the photoelectric transducer board, e.g., corners thereof, are prevented from becoming damaged, and the mechanical strength of the side plate of the casing is maintained. Therefore, reliability of the radiation detecting apparatus during use is increased.

The recess may comprise a cavity, which is concave as viewed in plan. If the corner of the photoelectric transducer board is displaced toward the cavity in order to bring two adjacent sides of the photoelectric transducer board into contact with respective inner wall surfaces of the side plate on both sides of the cavity, then the corner between the two adjacent sides is spaced from a bottom of the cavity by a minimum distance in a range from 1 mm to 5 mm.

Even if the sides of the photoelectric transducer board come into contact with the inner wall surfaces of the side plate, a gap remains between the corner of the photoelectric transducer board and the cavity. Thus, even if the corner of the photoelectric transducer board vibrates due to an impact that may occur if the radiation detecting apparatus is dropped onto the floor or is touched or hit by another object, the corner is not brought into contact with the bottom surface or inner wall surfaces of the cavity, and hence the photoelectric transducer board is prevented from becoming damaged upon vibration thereof.

The cavity may be defined by two side wall surfaces adjoining the respective inner wall surfaces, and a bottom surface interconnecting the two side wall surfaces. The corner and the bottom surface of the cavity may be spaced from each other by the minimum distance in the range from 1 mm to 5 mm.

The corner may have a single apex, and the single apex of the corner and the bottom surface of the cavity may be spaced from each other by the minimum distance in the range from 1 mm to 5 mm.

Alternatively, the corner may have at least two apexes, and one of the at least two apexes, which is closest to the bottom surface of the cavity, and the bottom surface may be spaced from each other by the minimum distance in the range from 1 mm to 5 mm.

The recess may comprise a cavity, which is concave as viewed in plan, and which also is concave as viewed in vertical cross section. The cavity may be defined between a first surface, which is closer to the upper plate, and a second surface, which is closer to the lower plate. The photoelectric transducer board may have a surface facing the upper plate and spaced from the first surface by a minimum distance, and a surface facing the lower plate and spaced from the second surface by a minimum distance, each of the minimum distances being in the range from 1 mm to 5 mm.

Accordingly, even if the sides of the photoelectric transducer board contact the inner wall surfaces of the side plate, a gap remains between the corner of the photoelectric transducer board and the cavity, e.g., the bottom surface thereof. In addition, a gap remains between the surface of the photoelectric transducer board that faces toward the upper plate and the first surface, and a gap also remains between the surface of the photoelectric transducer board that faces toward the lower plate and the second surface. Even if the corner of the photoelectric transducer board vibrates in directions across a plane thereof, due to an impact that may occur if the radiation detecting apparatus is dropped onto the floor or is touched or hit by another object, the corner is prevented from coming into contact with inner wall surfaces of the cavity, i.e., the bottom surface, the first surface, the second surface, etc., and hence the photoelectric transducer board is prevented from becoming damaged due to vibrations.

The radiation detecting apparatus may further comprise a first base plate disposed between the upper plate and the photoelectric transducer board and supporting the radiation detector thereon. The scintillator may be disposed on a surface of the photoelectric transducer board, which is remote from the first base plate. The first base plate has a thickness ta, the photoelectric transducer board has a thickness tb, the scintillator has a thickness tc, and the cavity has a height ha along a thickness direction of the photoelectric transducer board, wherein the thicknesses ta, tb, tc, and the height ha are related to each other by the inequality $tb < ha < (ta+tb+tc)$.

More specifically, the height of the cavity is greater than the thickness of the photoelectric transducer board, but is smaller than the sum of the thicknesses of the first base plate, the photoelectric transducer board, and the scintillator. Because of the above-described thickness relationship and also due to the gaps referred to above, if the photoelectric transducer board is displaced upon the radiation detecting apparatus being dropped onto the floor or touched or hit by another object, the corner of the photoelectric transducer board partially enters into the cavity, but is prevented from coming into contact or colliding with the side plate.

The photoelectric transducer board may have a transverse length, which is greater than a transverse length of the scintillator, and a longitudinal length, which is greater than a longitudinal length of the scintillator. Therefore, even if the photoelectric transducer board is displaced together with the scintillator if the radiation detecting apparatus is dropped onto the floor or is touched or hit by another object, the scintillator is prevented from coming into contact or colliding with the side plate.

The upper plate and the first base plate may be fixed to each other by an adhesive layer, and the first base plate and the photoelectric transducer board may be bonded to each other by a pressure-sensitive adhesive. Since the first base plate and the photoelectric transducer board are bonded to each other by the pressure-sensitive adhesive tape, the radiation detector can easily be replaced or repaired. Such a structure makes it easier for the photoelectric transducer board to move if the radiation detecting apparatus is dropped onto the floor or is touched or hit by another object. However, as described above, even if the photoelectric transducer board is displaced, the corner of the photoelectric transducer board partially enters into the cavity, while being prevented from coming into contact or colliding with the side plate. Therefore, even though the above structure allows the radiation detector to easily be replaced or repaired, reliability of the radiation detecting apparatus during use can be increased.

The radiation detecting apparatus may further comprise a second base plate disposed between the scintillator and the lower plate, and which supports the radiation detector thereon in coaction with the first base plate. The upper plate and the first base plate may be fixed to each other by an adhesive layer. The first base plate and the photoelectric transducer board may be bonded to each other by a pressure-sensitive adhesive. The second base plate and the scintillator may also be bonded to each other by a pressure-sensitive adhesive. Such a structure allows the radiation detector to easily be replaced or repaired, while also increasing reliability of the radiation detecting apparatus during use.

The first base plate preferably is made of a non-metal material, and the second base plate preferably is made principally from a non-metal material. Such non-metal materials enable the radiation detecting apparatus to be made lighter in weight.

According to the present invention, as described above, even if the radiation detecting apparatus is dropped onto the floor by mistake, or is touched or hit by another object while the radiation detecting apparatus is being carried, the photoelectric transducer board, e.g., a corner thereof, is prevented from being damaged, while at the same time, the mechanical strength of the side plate of the casing is maintained. Therefore, reliability of the radiation detecting apparatus during use can be increased.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Radiation detecting apparatus according to embodiments of the present invention will be described in detail below with reference to FIGS. 1 through 11. Various numerical ranges, which are referred to in the following description, should be interpreted as including numerical values at ends of the ranges as upper and lower limit values thereof.

Figure 1:
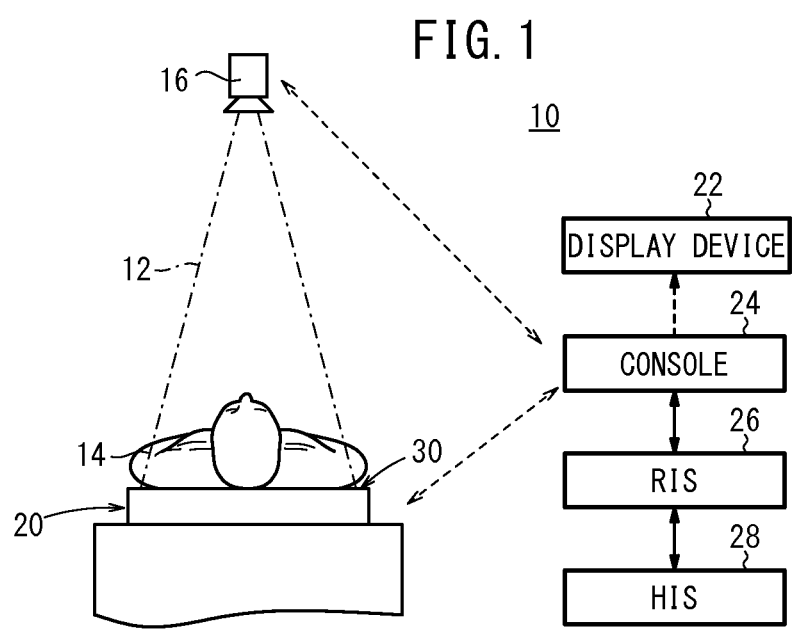
FIG. 1 is a schematic view, partially in block form, of a radiographic image capturing system, which incorporates therein a radiation detecting apparatus according to an embodiment of the present invention.

As shown in FIG. 1, a radiographic image capturing system 10 according to an embodiment of the present invention includes a radiation source 16 for applying a dose of radiation 12 to a subject 14 according to given image capturing conditions, a radiation detecting apparatus 20 for detecting radiation 12 that has passed through the subject 14, a display device 22 for displaying a radiographic image based on radiation 12 that is detected by the radiation detecting apparatus 20, and a console (controller) 24 for controlling the radiation source 16, the radiation detecting apparatus 20, and the display device 22. The console 24, the radiation source 16, the radiation detecting apparatus 20, and the display device 22 exchange signals via wireless communication, for example.

The console 24 is connected to a radiology information system (RIS) 26, which generally manages radiographic image information as well as other information handled by the radiological department of a hospital in which the radiographic image capturing system 10 is installed. The RIS 26 is connected to a hospital information system (HIS) 28, which generally manages medical information in the hospital.

Figure 2:
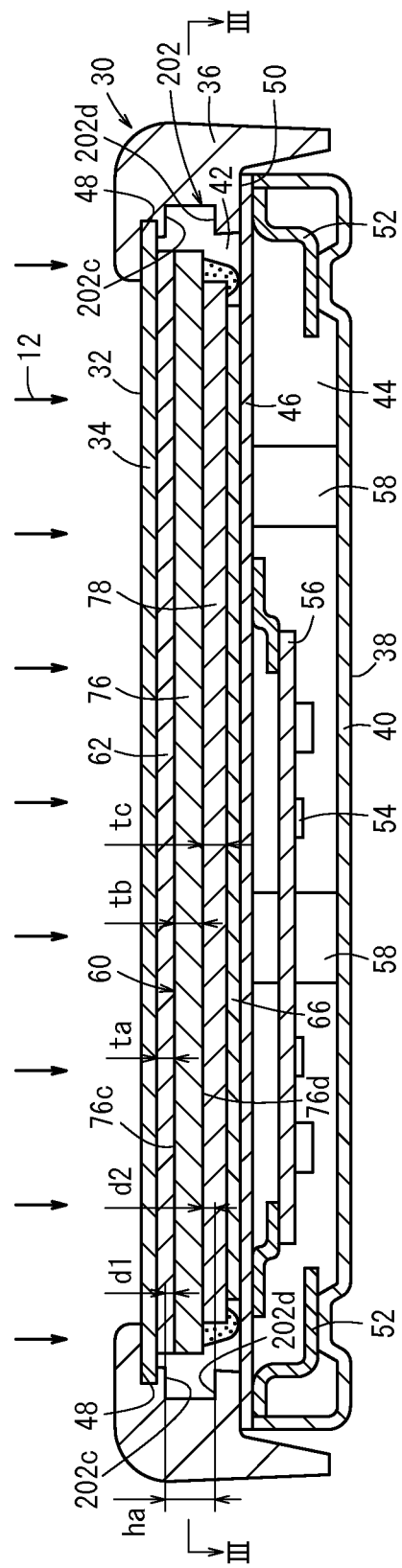
FIG. 2 is an enlarged cross-sectional view taken along line II-II of FIG. 3, showing structural details of the radiation detecting apparatus.

As shown in FIG. 2, the radiation detecting apparatus 20 includes a substantially cuboid casing 30 made of a material that is permeable to radiation 12. The casing 30 has a substantially planar first plate (upper plate) 34 providing an outer front surface (irradiated surface) 32 that is exposed to radiation 12, a frame (side plate) 36 providing side surfaces, a substantially planar second plate (lower plate) 40 providing an outer rear surface 38 remote from the front surface 32, and a chassis 46 attached to the frame 36 and disposed between the first plate 34 and the second plate 40, thereby dividing a storage space in the casing 30 into a first compartment 42 near the first plate 34 and a second compartment 44 near the second plate 40.

The frame 36 has an annular groove 48 defined in an inner wall thereof near the front surface 32 for receiving a peripheral edge of the first plate 34 fitted therein. The frame 36 also has an annular flat step 50 on an inner wall thereof substantially at a central position along the height or width of the frame 36. The chassis 46 has a peripheral edge, which is fastened by screws or an adhesive to the annular flat step 50. A joint 52, which is in the form of a plurality of joint members each having an L-shaped cross section or a single frame member having an L-shaped cross section, is fixed to the peripheral edge of the chassis 46 near the rear surface 38. The second plate 40 is joined to the joint 52. The joint 52, the peripheral edge of the chassis 46, and the flat step 50 of the frame 36 may be secured together by screws, for example. One or more circuit boards 56 having various electronic components 54 mounted thereon are disposed on a surface of the chassis 46 that faces the rear surface 38. The second plate 40 has an inner surface including a portion held against a portion of the joint 52, and which is fastened thereto by screws or an adhesive. A plurality of spacers 58 are disposed between and joined to the chassis 46 and the second plate 40. The spacers 58 provide a space or height between the chassis 46 and the second plate 40, which is large enough to house at least the circuit boards 56 in the second compartment 44. The spacers 58 also preserve the flatness of at least a central region of the second plate 40, which is positioned inwardly of the portion of the second plate 40 that is fastened to the joint 52.

A radiation detector 60 is disposed in the first compartment 42, which is surrounded by the first plate 34, the frame 36, and the chassis 46. More specifically, a first base plate 62, which supports the radiation detector 60 thereon, is fixed by a first adhesive layer 64 to an inner surface of the first plate 34, which faces away from the front surface 32 (see FIG. 5). A second base plate 66, which supports the radiation detector 60 thereon and which also reinforces the scintillator 78, is fixed by a second adhesive layer 68 to a surface of the chassis 46, which faces toward the first plate 34 (see FIG. 5). The radiation detector 60 is disposed between the first base plate 62 and the second base plate 66. The first base plate 62 has a thickness in a range up to 0.5 mm, whereas the second base plate 66 has a thickness in a range from 0.8 mm to 1.5 mm.

The radiation detector 60 converts radiation 12 that has passed through the subject 14 into radiographic image information, and outputs the radiographic image information as an analog electric signal to the console 24. The radiation detecting apparatus 20 also includes a battery 70, a cassette controller 72, and a transceiver 74 (see FIG. 6), in addition to the circuit boards 56 and the radiation detector 60. The battery 70, which serves as a power supply for the radiation detecting apparatus 20, supplies electric power to the radiation detector 60, the cassette controller 72, and the transceiver 74. The cassette controller 72 controls the radiation detector 60 upon electric power being supplied thereto from the battery 70. The transceiver 74 exchanges signals with the console 24, such signals being representative of information (radiographic image information) of radiation 12 detected by the radiation detector 60.

Figure 5:
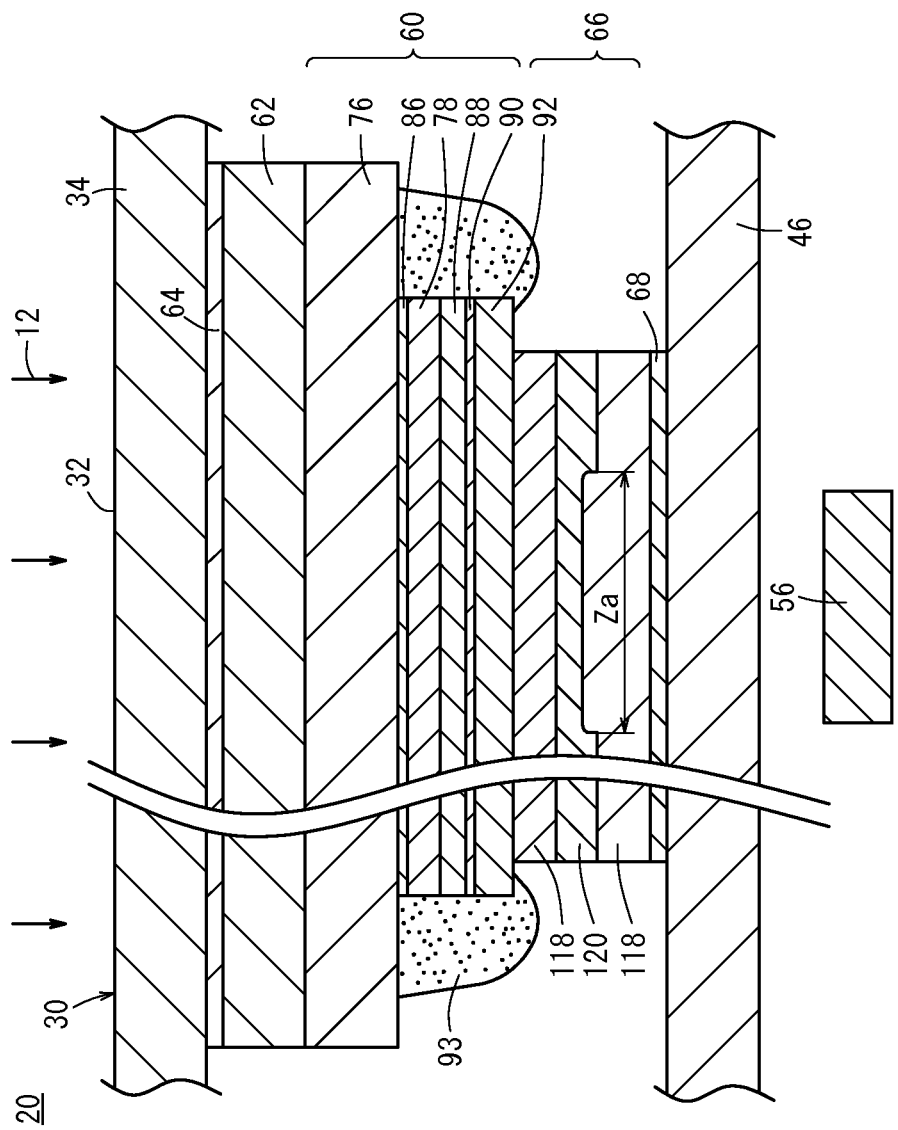
FIG. 5 is an enlarged fragmentary cross-sectional view of the radiation detecting apparatus.

As shown in FIGS. 2 and 5, the radiation detector 60 includes a substantially cuboid photoelectric transducer board 76 disposed closer to the front surface 32, and a scintillator 78 disposed closer to the rear surface 38. The scintillator 78 is made of a phosphor having a matrix of GOS ($Gd_2O_2S$:Tb), CsI:Tl, or the like, which converts radiation 12 that has passed through the subject 14 into visible light. The photoelectric transducer board 76 includes a photoelectric transducer layer 84 (see FIG. 6) for converting visible light from the scintillator 78 into an electric signal. The photoelectric transducer layer 84 includes an array of thin-film transistors 80 (see FIG. 6, hereinafter referred to as "TFTs 80"), and an array of solid-state detecting elements 82 (see FIG. 6, hereinafter also referred to as "pixels 82") made of amorphous silicon (a-Si) or the like.

Planar configurations of the frame 36, the photoelectric transducer board 76, etc., will be described below with reference to FIGS. 3, 4A and 4B.

Figure 3:
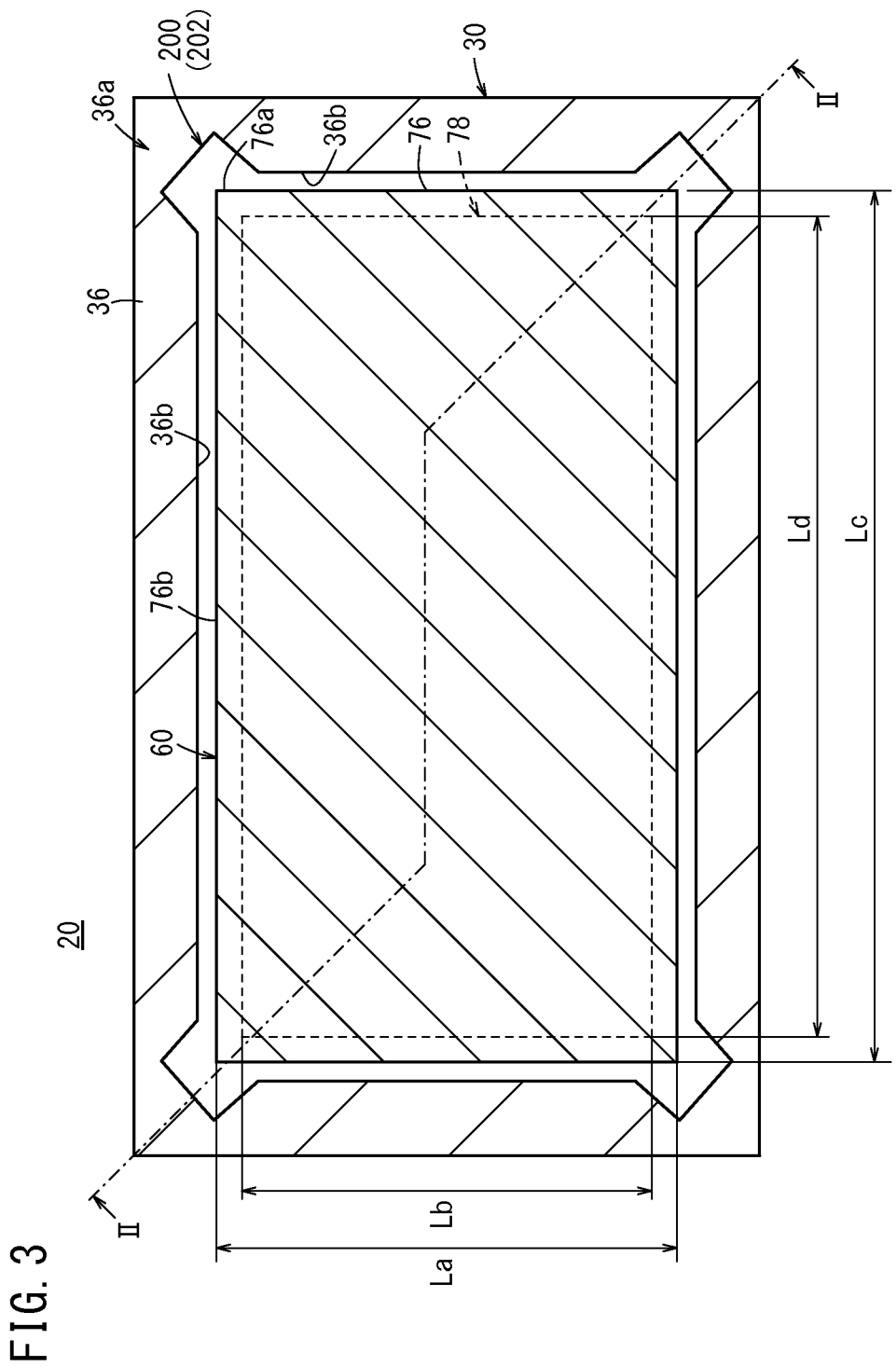
FIG. 3 is an enlarged cross-sectional view taken along line of FIG. 2.

As shown in FIG. 3, the frame 36 has recesses 200 defined therein, which face toward and are spaced from respective corners 76a of the photoelectric transducer board 76. More specifically, the recesses 200 are defined in respective corners 36a on an inner peripheral edge of the frame 36, in facing relation to the respective corners 76a of the photoelectric transducer board 76.

Each of the recesses 200 is in the form of a cavity 202, which is concave both as viewed in plan and in vertical cross section. As indicated by the two-dot-and-dash lines in FIG. 4A, if the corresponding corner 76a of the photoelectric transducer board 76 were displaced toward the cavity 202 in order to bring two adjacent sides 76b of the photoelectric transducer board 76 into contact with respective inner wall surfaces 36b of the frame 36 on both sides of the cavity 202, then the corner 76a between the sides 76b would be spaced from the bottom of the cavity 202 by a minimum distance da in a range from 1 mm to 5 mm. More specifically, the cavity 202 is defined by two side wall surfaces 202a adjoining the respective inner wall surfaces 36b, and a bottom surface 202b interconnecting the side wall surfaces 202a. The corner 76a of the photoelectric transducer board 76 and the bottom surface 202b of the cavity 202 are spaced from each other by the minimum distance da in the range from 1 mm to 5 mm. More specifically, as shown in FIG. 4A, the corner 76a of the photoelectric transducer board 76 has an apex 76t, which is spaced from the bottom surface 202b of the cavity 202 by the minimum distance da in the range from 1 mm to 5 mm. Alternatively, as shown in FIG. 4B, the corner 76a of the photoelectric transducer board 76 may have two or more apexes 76t, wherein one of the apexes 76t, which is closest to the bottom surface 202b of the cavity 202, is spaced from the bottom surface 202b by the minimum distance da in the range from 1 mm to 5 mm.

As shown in FIG. 2, the cavity 202 is defined between a first surface 202c, which is disposed closer to the first plate 34, and a second surface 202d, which is disposed closer to the second plate 40. The photoelectric transducer board 76 has a surface 76c facing toward the first plate 34 and which is spaced from the first surface 202c by a minimum distance d1, and another surface 76d facing toward the second plate 40 and which is spaced from the second surface 202d by a minimum distance d2. Each of the minimum distances d1, d2 is in a range from 1 mm to 5 mm.

If the thickness of the first base plate 62 is represented by ta, the thickness of the photoelectric transducer board 76 is represented by tb, the thickness of the scintillator 78 is represented by tc, and the height of the cavity 202 along the thickness direction of the photoelectric transducer board 76 is represented by ha, then the dimensions are related to each other by the inequality $tb<ha<(ta+tb+tc)$.

As shown in FIG. 3, the photoelectric transducer board 76 has a vertical or transverse length La, which is greater than the vertical or transverse length Lb of the scintillator 78. The photoelectric transducer board 76 also has a horizontal or longitudinal length Lc, which is greater than the horizontal or longitudinal length Ld of the scintillator 78.

As shown in FIG. 5, the scintillator 78 and the photoelectric transducer board 76 are joined to each other with an intermediate layer 86 interposed therebetween. The intermediate layer 86 has a thickness in a range from 10 μm to 50 μm, and a haze level in the range from 3% to 50%. The intermediate layer 86 should preferably be made of an adhesive containing a filler. The adhesive preferably is a hot-melt adhesive, a reactive hot-melt adhesive, or a thermosetting adhesive. A hot-melt adhesive is particularly preferable, in that such a hot-melt adhesive can level out surface irregularities of the photoelectric transducer board 76.

The filler may be an inorganic material such as alumina, silica, titanium oxide, zirconium oxide, yttrium oxide, or the like, or an organic material such as highly cross-linked acrylic resin, highly cross-linked polystyrene, melamine-formaldehyde resin, silicone resin, or the like. Such filler materials may be used alone or in combination.

The intermediate layer 86 is not limited to the above adhesives, but may be a pressure-sensitive adhesive, such as a polyacrylic pressure-sensitive adhesive, a silicone rubber pressure-sensitive adhesive, a polyvinyl butyl ether pressure-sensitive adhesive, a polyisobutylene pressure-sensitive adhesive, a natural rubber pressure-sensitive adhesive, or the like. Such a pressure-sensitive adhesive can be peeled off from a surface after having been bonded to the surface.

Between the scintillator 78 and the second base plate 66, there are disposed a light reflecting layer 88 for reflecting light, an antistatic electrically conductive layer 90, and a support layer 92, which are arranged in this order from the scintillator 78 toward the second base plate 66. The photoelectric transducer board 76, the scintillator 78, the light reflecting layer 88, the electrically conductive layer 90, and the support layer 92 are integrally combined with each other by an ultraviolet-curable adhesive 93.

The support layer 92, which may comprise a plastic substrate, a silicon substrate, a carbon substrate, or the like, has a thickness in a range from 0.15 mm to 0.30 mm. The support layer 92 may be made of a white resin material, which is produced by mixing a resin material such as polyethylene terephthalate (PET), polycarbonate, polyethylene naphthalate, or the like, with a pigment of titanium oxide, aluminum oxide, or the like, or any of various types of metal particles or metal foils.

The electrically conductive layer 90 preferably is made of a metal material, a metal oxide material, or an electrically conductive organic material. The electrically conductive layer 90 has a thickness of 5 μm or smaller. The metal material should be magnesium, magnesium alloy, aluminum alloy, or the like, as such materials possess low radiation absorptance. The metal oxide material preferably is composed of acicular microparticles of $SnO_2$ (Sb-doped). The electrically conductive organic material preferably is an electrically conductive carbon film or the like.

The light reflecting layer 88 is a layer containing a light reflecting material. Examples of suitable light reflecting materials include white pigments of $Al_2O_3$, $ZrO_2$, MgO, $BaSO_4$, $SiO_2$, ZnS, ZnO, $CaCO_3$, $Sb_2O_3$, $Nb_2O_5$, $2PbCO_3 \cdot Pb(OH)_2$, $PbF_2$, $BiF_3$, $Y_2O_3$, YOCl, MIIFX (where MII refers to at least one of Ba, Sr, and Ca, and X refers to at least one of Cl and Br), lithopone ($BaSO_4$+ZnS), magnesium silicate, basic silicate sulfate, basic phosphate, and aluminum silicate; various types of metal particles or metal foils; and hollow polymer particles. The above materials may be used alone or in combination. Among the above materials, $Al_2O_3$, $ZrO_2$, $PbF_2$, $BiF_3$, $Y_2O_3$, and YOCl are particularly preferable, due to the higher refractive indices exhibited thereby. The light reflecting layer 88 has a thickness in a range from 50 μm to 80 μm.

The support layer 92 and the second base plate 66 are bonded to each other by a non-illustrated double-sided pressure-sensitive adhesive tape. Similarly, the photoelectric transducer board 76 and the first base plate 62 are bonded to each other by a non-illustrated double-sided pressure-sensitive adhesive tape. The double-sided pressure-sensitive adhesive tapes include a pressure-sensitive adhesive that can be peeled off from a surface after it has been bonded to the surface. Therefore, the radiation detector 60 can easily be detached from the radiation detecting apparatus 20, so as to enable repairs to be performed thereon. However, the support layer 92 and the second base plate 66 may be bonded securely to each other by an adhesive. Similarly, the photoelectric transducer board 76 and the first base plate 62 may be bonded securely to each other by an adhesive.

In the present embodiment, the radiation detector 60 is a face-side readout ISS (Irradiation Side Sampling) type of radiation detector, including the photoelectric transducer board 76 and the scintillator 78, which are arranged successively along the direction in which radiation 12 is applied, wherein the photoelectric transducer board 76 closer to the first plate 34 converts light emitted from the scintillator 78 into electric charges in order to read radiographic image information. However, the radiation detector 60 may also be a reverse-side readout PSS (Penetration Side Sampling) type of radiation detector, in which the photoelectric transducer board 76 positioned behind the scintillator 78 converts light emitted from the scintillator 78 into electric charges in order to read radiographic image information.

The scintillator 78 normally emits more intensive light from the front surface thereof, which is irradiated with radiation 12, than from the rear surface thereof. A face-side readout type radiation detector 60 according to the present embodiment allows light emitted from the scintillator 78 to reach the photoelectric transducer board 76, i.e., the photoelectric transducer layer 84, in a shorter period of time than a reverse-side readout type radiation detector 60. Further, since light emitted from the scintillator 78 is prevented from being scattered and attenuated more effectively, the resolution of the produced radiographic image information is increased.

Circuit details of the radiation detecting apparatus 20 will be described below with reference to FIGS. 6 and 7.

Figure 6:
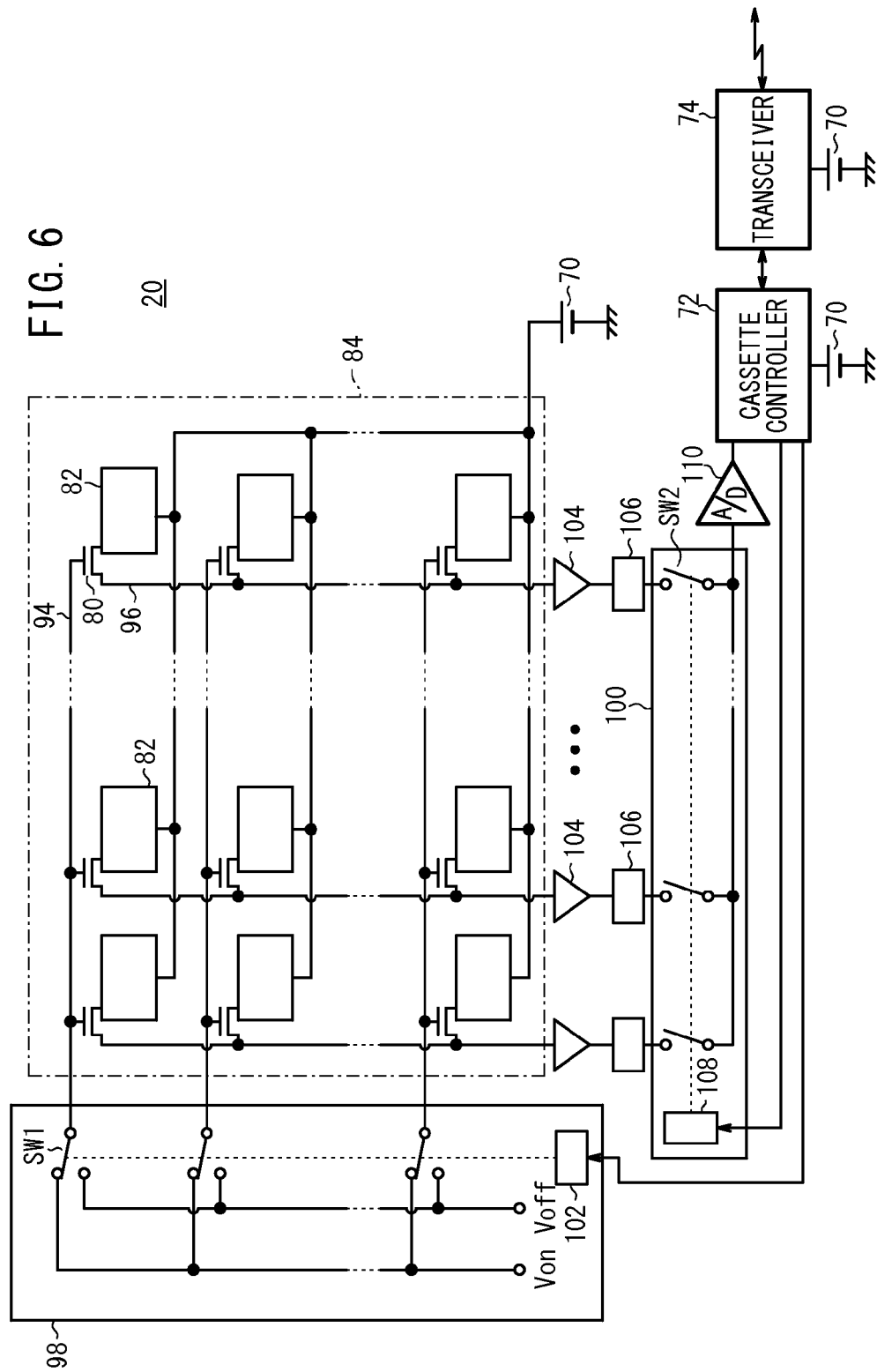
FIG. 6 is a circuit diagram, partially in block form, of the radiation detecting apparatus.

As shown in FIG. 6, the radiation detecting apparatus 20 comprises an array of TFTs 80 arranged in rows and columns, and a photoelectric transducer layer 84 including pixels 82, and made of a material such as a-Si or the like for converting visible light into electric signals. The photoelectric transducer layer 84 is disposed on the array of TFTs 80. In a case where radiation is applied to the radiation detecting apparatus 20, the pixels 82 generate electric charges by converting visible light into analog electric signals, which are stored therein as generated electric charges. Then, in a case where the TFTs 80 are turned on along each row at a time, the stored electric charges are read from the pixels 82 as an image signal.

The TFTs 80 are connected respectively to the pixels 82. Gate lines 94, which extend parallel to the rows, and signal lines 96, which extend parallel to the columns, are connected to the TFTs 80. The gate lines 94 are connected to a line scanning driver 98, and the signal lines 96 are connected to a multiplexer 100. The gate lines 94 are supplied with control signals Von, Voff for turning on and off the TFTs 80 along the rows from the line scanning driver 98. The line scanning driver 98 includes a plurality of switches SW1 for switching between the gate lines 94, and an address decoder 102 for outputting a selection signal for selecting one of the switches SW1 at a time. The address decoder 102 is supplied with an address signal from the cassette controller 72.

The signal lines 96 are supplied with electric charges stored in the pixels 82 through the TFTs 80 arranged in the columns. The electric charges supplied to the signal lines 96 are amplified by amplifiers 104, which are connected respectively to the signal lines 96. The amplifiers 104 are connected through respective sample and hold circuits 106 to the multiplexer 100. The multiplexer 100 includes a plurality of switches SW2 for successively switching between the signal lines 96, and an address decoder 108 for outputting a selection signal for selecting one of the switches SW2 at a time. The address decoder 108 is supplied with an address signal from the cassette controller 72. The multiplexer 100 has an output terminal connected to an A/D converter 110. A radiographic image signal, which is generated by the multiplexer 100 based on the electric charges from the sample and hold circuits 106, is converted by the A/D converter 110 into a digital image signal representing radiographic image information, which is supplied to the cassette controller 72.

In FIG. 6, the line scanning driver 98, the multiplexer 100, the amplifiers 104, the sample and hold circuits 106, and the A/D converter 110 are included in the electronic components 54. Portions of the gate lines 94, which extend from the line scanning driver 98 to the photoelectric transducer layer 84, as well as portions of the signal lines 96, which extend from the photoelectric transducer layer 84 to the amplifiers 104, are included in the photoelectric transducer board 76.

The TFTs 80, which function as switching devices, may be combined with another image capturing device such as a CMOS (Complementary Metal-Oxide Semiconductor) image sensor or the like. Alternatively, the TFTs 80 may be replaced with a CCD (Charge-Coupled Device) image sensor for shifting and transferring electric charges with shift pulses, which correspond to gate signals in the TFTs.

Figure 7:
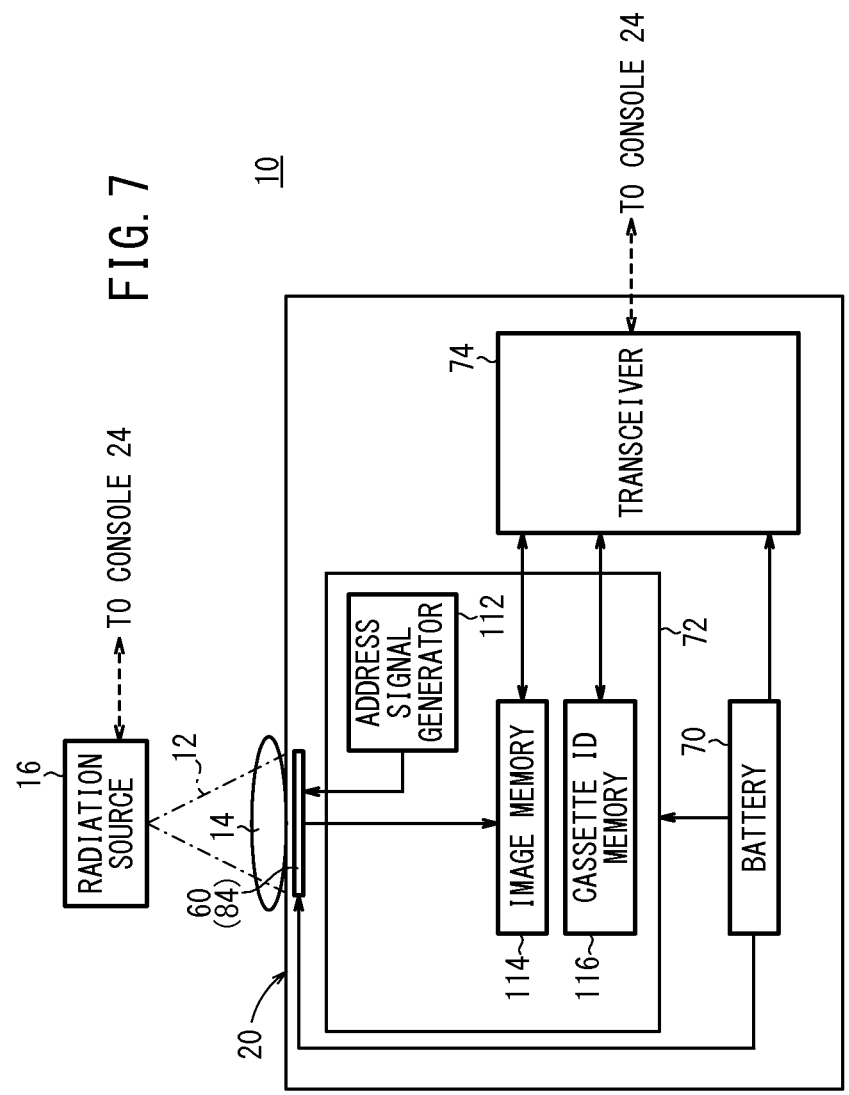
FIG. 7 is a block diagram of the radiation detecting apparatus.

As shown in FIG. 7, the cassette controller 72 of the radiation detecting apparatus 20 includes an address signal generator 112, an image memory 114, and a cassette ID memory 116.

The address signal generator 112 supplies address signals to the address decoder 102 of the line scanning driver 98 and to the address decoder 108 of the multiplexer 100 shown in FIG. 6. The image memory 114 stores radiographic image information detected by the radiation detector 60. The cassette ID memory 116 stores cassette ID information for identifying the radiation detecting apparatus 20.

The transceiver 74 sends the cassette ID information, which is stored in the cassette ID memory 116, and the radiographic image information, which is stored in the image memory 114, to the console 24 via a wireless communication link.

The first base plate 62 is made of a material having a specific gravity of 2.8 or smaller for reducing the overall weight of the radiation detecting apparatus 20. The material of the first base plate 62 is any one of a composite material including carbon fibers, cellulose fibers, glass fibers, engineering plastics, and biomass plastics.

As shown in FIG. 5, the second base plate 66 comprises two first members 118 and a second member 120, which have different functions respectively. As with the first base plate 62, each of the first members 118 is made of a material having a specific gravity of 2.8 or smaller for reducing the overall weight of the radiation detecting apparatus 20. The material of the first members 118 is any one of a composite material including carbon fibers, cellulose fibers, glass fibers, engineering plastics, and biomass plastics. The second member 120 is made of a metal material for attenuating scattered rays from radiation 12 that passes through the casing 30, e.g., scattered rays from behind the second base plate 66. As shown in FIG. 5, the second member 120 is sandwiched between and integrally combined with the first members 118.

The first base plate 62 and the first members 118 of the second base plate 66 may be made of the same material or different materials.

The aforementioned composite material containing carbon fibers is a carbon-fiber-reinforced plastic (CFRP), a composite material of a sandwiched structure having a preform of carbon fibers encased in a foaming material and then impregnated with a resin, or a composite material of CFRP coated with a foaming material. The aforementioned composite material containing cellulose fibers is a composite material containing cellulose microfibril fibers. The aforementioned composite material containing glass fibers is a glass-fiber-reinforced plastic (GFRP).

The first base plate 62 preferably is made of highly rigid carbon of PAN (polyacrylonitrile) carbon fibers, the thermal conductivity of which is relatively low, in order to prevent the subject (patient) 14 from feeling heat through the first base plate 62 in a case where the electronic components 54, etc., of the radiation detecting apparatus 20 are heated. The first members 118 of the second base plate 66 preferably are made of highly rigid carbon made up of pitch-based carbon fibers, the thermal conductivity of which is higher than the PAN carbon fibers, in order to effectively radiate heat outwardly from the radiation detecting apparatus 20 through the chassis 46.

The engineering plastics include polyamide (PA), polyacetal (POM), polycarbonate (PC), modified polyphenylene ether (m-PPE, modified PPE), polybutylene terephthalate (PBT), polyethylene terephthalate (PET), glass-fiber-reinforced polyethylene terephthalate (GF-PET), ultra high molecular weight polyethylene (UHPE), syndiotactic polystyrene (SPS), cyclic polyolefin (COP), polyphenylene sulfide (PPS), polysulfone (PSF), amorphous polyarylate (PAR), polyether sulfone (PES), liquid crystal polyester (LCP), polyetheretherketone (PEEK), polyimide (PI), polyetherimide (PEI), epoxy (EP), etc.

If the thickness of the second member 120 of the second base plate 66 is constant, then the attenuation distribution of scattered rays from behind becomes irregular. More specifically, since scattered rays from behind are attenuated by metal layers of the electrically conductive pattern of the circuit boards 56, areas of the second member 120, which are aligned with the circuit boards 56, and other areas of the second member 120 attenuate the scattered rays to different degrees. As a result, noise images produced by attenuated scattered rays, which are applied to the scintillator 78, correspond to profiles of the circuit boards 56, and hence are easy to notice and tend to make the captured radiographic image lower in quality. Such problems do not arise if the second member 120 is capable of absorbing all of the scattered rays. However, in this case, the second base plate 66 would have to be made of a heavy material such as lead or the like, and thus, depending on the size of the second base plate 66, the radiation detecting apparatus 20 could not be reduced in weight.

Figure 8:
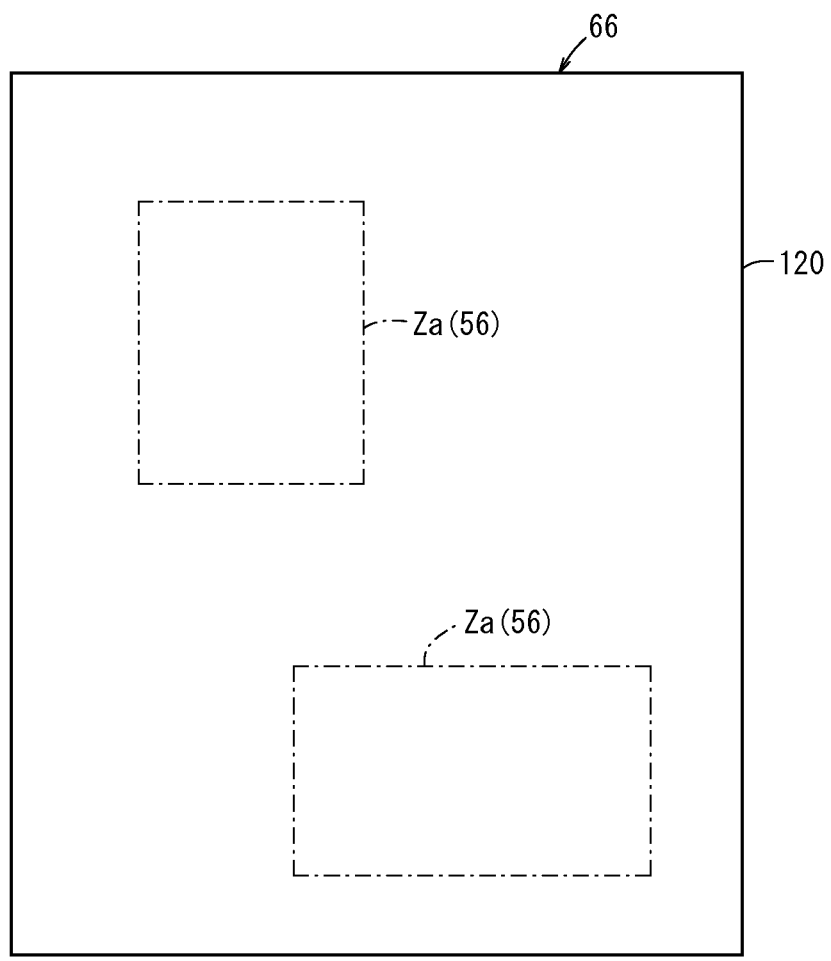
FIG. 8 is a view showing areas of a second member of a second substrate onto which circuit boards are projected.
Figure 9A:
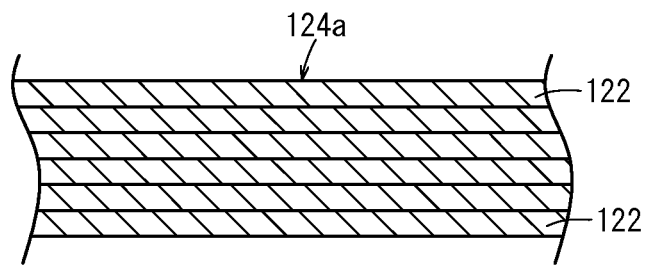
FIGS. 9A through 9D are fragmentary cross-sectional views showing an example of a process for fabricating the second member of the second substrate.
Figure 9B:
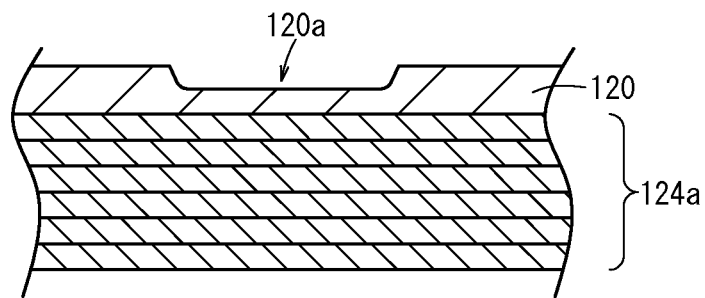
Figure 9C:
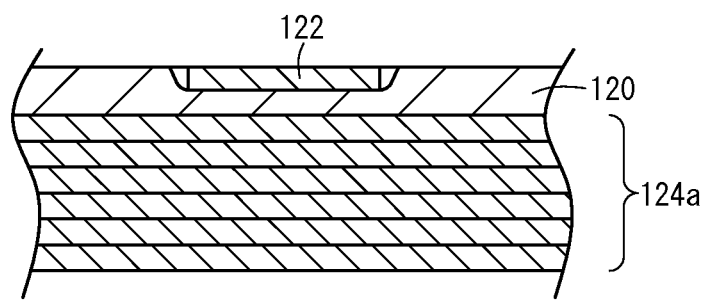
Figure 9D:
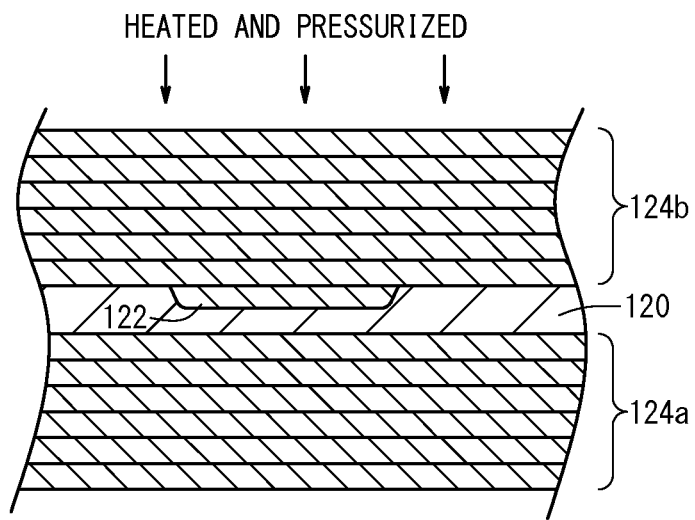

According to the present embodiment, the thickness of the second member 120 of the second base plate 66 is changed at locations where the circuit boards 56 are positioned. For example, as shown in FIG. 8, the second member 120 has areas Za toward which the circuit boards 56 project, and such areas Za have a smaller thickness than other areas of the circuit board 56.

The metal material of the second member 120 of the second base plate 66 may be aluminum, silver, copper, or the like, and preferably is the same as the metal material of the electrically conductive pattern of the circuit boards 56. For example, since the electrically conductive pattern of the circuit boards 56 is produced by selectively etching a copper foil, the metal material of the second member 120 of the second base plate 66 preferably is copper.

The areas Za of the second member 120 preferably are thinner than other areas of the circuit board 56 by an amount equal to the thickness of the electrically conductive pattern of the circuit boards 56. If each of the circuit boards 56 comprises a stacked assembly of electrically conductive patterns, then the areas Za of the second member 120 should preferably be thinner than other areas of the circuit board 56 by an amount equal to the thickness of the stacked assembly of electrically conductive patterns.

Since the thickness of the areas Za of the second member 120, which correspond to the circuit boards 56, is reduced, the attenuation distribution of scattered rays from behind is made uniform over the entirety of the second member 120. Accordingly, noise images produced by attenuated scattered rays that are applied to the scintillator 78 are of a constant level as a whole, and hence are not easy to notice. Further, since the noise images are constant in level, the noise images can easily be removed by subsequent simple image processing, such as an offsetting process.

A process of fabricating the second base plate 66 will be described below with reference to FIGS. 9A through 9D. A first stacked assembly 124a (see FIG. 9A) comprises a plurality of preforms 122 made of carbon fibers. A second member 120 in the form of a metal foil, a metal film, a metal sheet, or the like is placed on the first stacked assembly 124a (see FIG. 9B). A preform 122 of carbon fibers is placed on a thinner portion 120a of the second member 120, thereby making the upper surface of the second member 120 flat (see FIG. 9C). Then, a second stacked assembly 124b, which comprises a plurality of preforms 122 made of carbon fibers, is placed on the second member 120 (see FIG. 9D). Thereafter, the first stacked assembly 124a, the second member 120, and the second stacked assembly 124b are heated and pressurized (see FIG. 9D), thereby producing the second base plate 66.

As shown in FIG. 2, the first plate 34 of the casing 30 may be made of the same material as the first base plate 62, and the second plate 40 of the casing 30 may be made of the same material as the first member 118 of the second base plate 66. The chassis 46 may be made of a material having a specific gravity of 2.8 or smaller, for thereby reducing the overall weight of the radiation detecting apparatus 20. More specifically, the material of the chassis 46 may be a metal material such as aluminum, aluminum alloy, magnesium, magnesium alloy, or the like.

The frame 36 of the casing 30 may be made of a synthetic resin or the like in order to enable the radiation detector 60 to be repaired, serviced, or replaced with ease. More specifically, the frame 36 can be elastically deformed to allow the first plate 34 and the first base plate 62 to easily be removed from the frame 36, while also enabling the radiation detector 60 to be removed with ease. The frame 36 can also be elastically deformed to facilitate installation of such components.

Figure 4A:
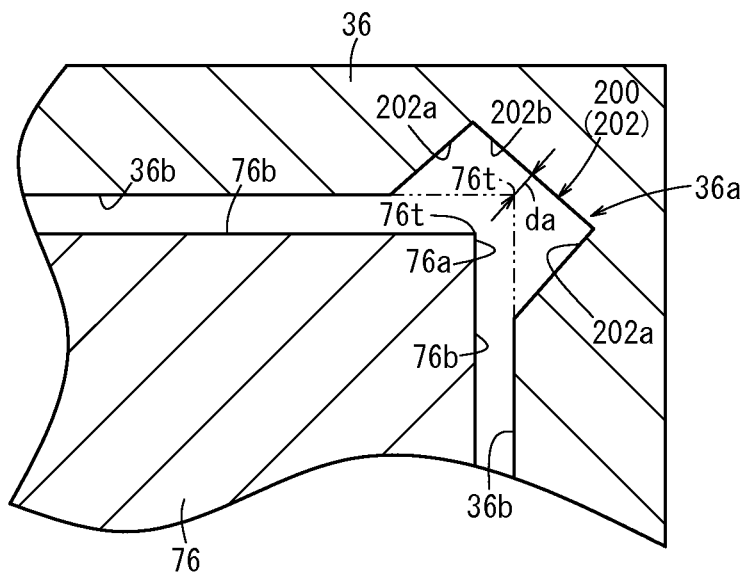
FIGS. 4A and 4B are enlarged cross-sectional views each showing a positional relationship between a corner of a photoelectric transducer board and a recess defined in a frame.
Figure 4B:
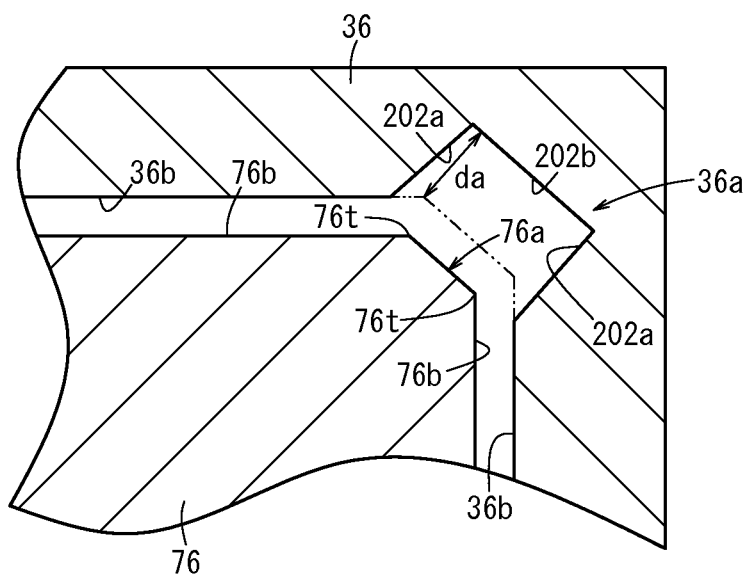

According to the present embodiment, as shown in FIGS. 3, 4A and 4B, the frame 36 has recesses 200 defined in portions thereof that face toward respective corners 76a of the photoelectric transducer board 76, the recesses 200 being concave in directions away from the corners 76a. More specifically, the recesses 200 are defined in respective corners 36a on the inner peripheral edge of the frame 36, in facing relation to the respective corners 76a of the photoelectric transducer board 76. Therefore, the mechanical strength of the frame 36, which is required to connect the first plate 34 and the second plate 40, is not lowered. Since the recesses 200 are concave in directions away from the corners 76a of the photoelectric transducer board 76, even if the radiation detecting apparatus 20 is dropped by mistake onto the floor, or is touched or hit by another object while the radiation detecting apparatus 20 is being carried, only the sides 76b of the photoelectric transducer board 76 are likely to contact the sides, i.e., the inner wall surfaces 36b, of the frame 36, and the corners 76a of the photoelectric transducer board 76 do not come into contact with or impinge on the frame 36. Even if some of the sides 76b of the photoelectric transducer board 76 are brought into contact with portions of the inner wall surfaces 36b of the frame 36, the photoelectric transducer board 76 is supported by two inner wall surfaces 36b at a time, and hence the overall weight of the photoelectric transducer board 76 is not concentrated on one local region of the frame 36. Consequently, the photoelectric transducer board 76 is free of risks of damage caused by the sides, i.e., the inner wall surfaces 36b, of the frame 36.

More specifically, according to the present embodiment, even if the radiation detecting apparatus 20 is dropped by mistake onto the floor, or is touched or hit by another object while the radiation detecting apparatus 20 is being carried, the photoelectric transducer board 76, e.g., the corners 76a thereof, are prevented from becoming damaged and the mechanical strength of the frame 36 of the casing 30 is maintained. Therefore, reliability of the radiation detecting apparatus 20 during use is increased.

Each of the recesses 200 is in the form of a cavity 202, which is concave as viewed in plan. As indicated by the two-dot-and-dash lines in FIG. 4A, if the corresponding corner 76a of the photoelectric transducer board 76 were displaced toward the cavity 202 in order to bring two adjacent sides 76b of the photoelectric transducer board 76 into contact with respective inner wall surfaces 36b of the frame 36 on both sides of the cavity 202, the corner 76a between the sides 76b would become spaced from the bottom of the cavity 202 by the minimum distance da in the range from 1 mm to 5 mm. Even if the sides 76b of the photoelectric transducer board 76 come into contact with the inner wall surfaces 36b of the frame 36, a gap remains between the corner 76a of the photoelectric transducer board 76 and the cavity 202. Further, even if the corner 76a of the photoelectric transducer board 76 vibrates due to an impact that may occur if the radiation detecting apparatus 20 is dropped onto the floor or is touched or hit by another object, the corner 76a is not brought into contact with the bottom surface 202b and inner wall surface of the cavity 202, and hence the photoelectric transducer board 76 is prevented from becoming damaged upon vibration thereof.

In particular, as shown in FIG. 2, the cavity 202 is defined between the first surface 202c, which is disposed closer to the first plate 34, and the second surface 202d, which is disposed closer to the second plate 40. The surface 76c of the photoelectric transducer board 76, which faces toward the first plate 34 of the photoelectric transducer board 76, is spaced from the first surface 202c by the minimum distance d1, and the surface 76d, which faces toward the second plate 40, is spaced from the second surface 202d by the minimum distance d2. Each of the minimum distances d1, d2 is in the range from 1 mm to 5 mm. Even if the sides 76b of the photoelectric transducer board 76 come into contact with the inner wall surfaces 36b of the frame 36, a gap remains between the corner 76a of the photoelectric transducer board 76 and the cavity 202, i.e., the bottom surface 202b of the cavity 202. In addition, a gap remains between the surface 76c of the photoelectric transducer board 76, which faces the first plate 34, and the first surface 202c. A gap also remains between the surface 76d of the photoelectric transducer board 76, which faces the second plate 40, and the second surface 202d. Even if the corner 76a of the photoelectric transducer board 76 vibrates in directions across the plane of the photoelectric transducer board 76, due to an impact that may occur if the radiation detecting apparatus 20 is dropped onto the floor or is touched or hit by another object, the corner 76a is prevented from contacting the inner wall surfaces of the cavity 202, i.e., the bottom surface 202b, the first surface 202c, the second surface 202d, etc., and thus the photoelectric transducer board 76 is prevented from becoming damaged upon vibration thereof.

According to the present embodiment, the thickness ta of the first base plate 62, the thickness tb of the photoelectric transducer board 76, the thickness tc of the scintillator 78, and the height ha of the cavity 202 along the thickness direction of the photoelectric transducer board 76 are related to each other by the inequality:

$$tb < ha < (ta+tb+tc).$$

More specifically, the height ha of the cavity 202 is greater than the thickness tb of the photoelectric transducer board 76, but is smaller than the sum of the thickness ta of the first base plate 62, the thickness tb of the photoelectric transducer board 76, and the thickness tc of the scintillator 78. Because of the above thickness relationship, and also the gaps referred to above, if the photoelectric transducer board 76 is displaced upon the radiation detecting apparatus 20 being dropped onto the floor or touched or hit by another object, the corner 76a of the photoelectric transducer board 76 partially enters into the cavity 202, but is prevented from coming into contact or colliding with the frame 36.

In particular, as shown in FIG. 3, the vertical or transverse length La of the photoelectric transducer board 76 is greater than the vertical or transverse length Lb of the scintillator 78, and the horizontal or longitudinal length Lc of the photoelectric transducer board 76 is greater than the horizontal or longitudinal length Ld of the scintillator 78. Therefore, even if the photoelectric transducer board 76 is displaced together with the scintillator 78, which may occur if the radiation detecting apparatus 20 is dropped onto the floor or is touched or hit by another object, the scintillator 78 is prevented from coming into contact or colliding with the frame 36.

Furthermore, according to the present embodiment, as shown in FIG. 2, the first plate 34 and the first base plate 62 are secured to each other by the first adhesive layer 64, and the first base plate 62 and the photoelectric transducer board 76 are bonded to each other by a double-sided pressure-sensitive adhesive tape. Since the first base plate 62 and the photoelectric transducer board 76 are bonded to each other by a double-sided pressure-sensitive adhesive tape, the radiation detector 60 can easily be replaced or repaired. Such a structure makes it easy for the photoelectric transducer board 76 to move if the radiation detecting apparatus 20 is dropped onto the floor or is touched or hit by another object. However, as described above, even if the photoelectric transducer board 76 is displaced, the corner 76a of the photoelectric transducer board 76 partially enters into the cavity 202, but is prevented from contacting or colliding with the frame 36. Therefore, even though the above structure allows the radiation detector 60 to easily be replaced or repaired, reliability of the radiation detecting apparatus 20 during use is increased.

As described above, even if the radiation detecting apparatus 20 according to the present embodiment is dropped onto the floor, or is touched or hit by another object while the radiation detecting apparatus 20 is being carried, the photoelectric transducer board 76, e.g., the corners 76a thereof, are prevented from being damaged, and the mechanical strength of the frame 36 of the casing 30 is maintained. Therefore, reliability of the radiation detecting apparatus 20 during use is increased.

According to the present embodiment, moreover, the second base plate 66 on the rear side of the radiation detector 60 includes the first member 118 and the second member 120, which have different functions, respectively. The first member 118 is made of a material for reducing the weight of the radiation detector 60, whereas the second member 120 is made of a metal material for attenuating scattered rays. Therefore, the second base plate 66 is effective to reduce the weight of the radiation detector 60 as well as to attenuate scattered rays applied to the scintillator 78, thereby reducing noise images that are produced by such scattered rays.

The radiation detecting apparatus 20 does not require a single metal plate or a stacked assembly of metal plates made of different materials depending on the transmittance or scattering probability of radiation, but rather, the radiation detecting apparatus 20 comprises the second base plate 66 including the first member 118 and the second member 120. Therefore, the number of steps required to manufacture the radiation detecting apparatus 20 is reduced, and the overall thickness of the radiation detecting apparatus 20 is not increased. Since a lead plate is not included in the radiation detecting apparatus 20, the radiation detecting apparatus 20 is reduced in weight. Since the second base plate 66, which supports the radiation detector 60 and reinforces the mechanical strength of the scintillator 78, doubles as a member for attenuating scattered rays, a dedicated base plate for attenuating scattered rays is not required in the radiation detecting apparatus 20, so that the radiation detecting apparatus 20 can be made lower in profile with a reduced thickness.

As described above, the radiation detecting apparatus 20 according to the present embodiment is capable of reducing the adverse effects of scattered rays, is reduced in weight, and is low in profile with a reduced thickness.

The metal material of the second member 120 is the same as the metal material of the electrically conductive patterns of the circuit boards 56, which are disposed behind the second base plate 66. The metal material of the second member 120 and the metal material of the electrically conductive patterns of the circuit boards 56 are thus effective to attenuate scattered rays applied to the scintillator 78.

In addition, the thickness of the second member 120 is changed depending on the position of the circuit boards 56, so as to make noise images produced by the attenuated scattered rays, which are applied to the scintillator 78, constant in level as a whole. In a case where radiographic image information is generated by the radiation detecting apparatus 20, the noise levels are not easily noticed in the radiographic image information, and hence the image quality of an image represented by the radiographic image information is prevented from being lowered by noise.

The present invention is not limited to the radiation detecting apparatus 20 according to the above embodiment, but various changes and modifications may be made to the radiation detecting apparatus 20 without departing from the essence of the invention.

Figure 10:
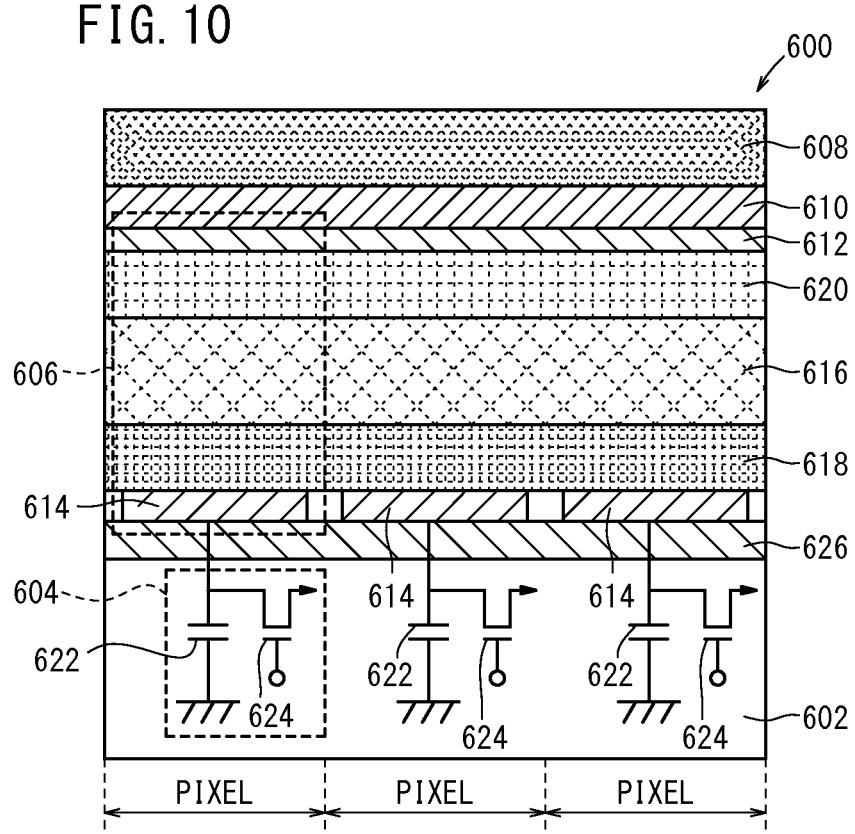
FIG. 10 is an enlarged cross-sectional view, partially omitted from illustration, of a modified radiation detector according to a modification of the present invention.
Figure 11:
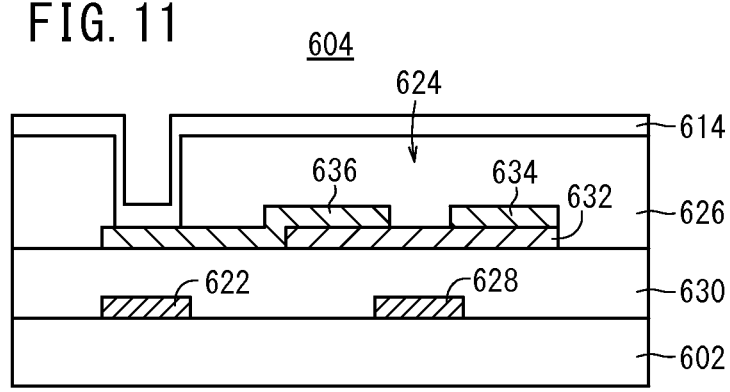
FIG. 11 is an enlarged cross-sectional view, partially omitted from illustration, of a signal output unit of the modified radiation detector.

FIGS. 10 and 11 show a modified radiation detector 600 according to a modification of the present invention. FIG. 10 is an enlarged cross-sectional view, partially omitted from illustration, of the modified radiation detector 600, and showing three pixel regions thereof.

As shown in FIG. 10, the radiation detector 600 includes a plurality of signal output units 604, a plurality of sensors 606, and a scintillator 608, which are disposed successively on an insulative substrate 602. The signal output units 604 and the sensors 606 make up respective pixels. The pixels are arrayed in rows and columns on the substrate 602, with the signal output unit 604 and the sensor 606 being superposed one on the other in each pixel.

The scintillator 608 is disposed over the sensors 606 with a transparent insulating film 610 interposed therebetween. The scintillator 608 includes a deposited layer of phosphor for converting radiation 12, which is applied downwardly in FIG. 10, into light, and emitting the light. Emitted light from the scintillator 608 has a wavelength range, which is preferably a visible wavelength range from 360 nm to 830 nm. If the radiation detector 600 is intended to capture monochromatic images, then the wavelength range of light emitted from the scintillator 608 preferably includes a wavelength range of green light.

If the radiation 12 comprises X-rays, then the phosphor of the scintillator 608 should preferably include cesium iodide (CsI), and more preferably, CsI(Tl) (thallium-doped cesium iodide), which emits light in a wavelength spectrum ranging from 420 nm to 700 nm upon being irradiated with X-rays. The visible wavelength range of CsI(Tl) has a peak wavelength of 565 nm.

The scintillator 608 may be formed by evaporating columnar crystalline CsI(Tl) onto a base, for example. For forming the scintillator 608 by way of evaporation, the base onto which CsI(Tl) is to be evaporated frequently is made of aluminum, in view of facilitating X-ray transmittance and reducing costs. However, the material of the base is not limited to aluminum. If the scintillator 608 is made of GOS, then the scintillator 608 may be formed by coating the surface of a TFT active matrix substrate with GOS. Alternatively, the scintillator 608 may be formed by coating a resin base with GOS, which is then bonded to a TFT active matrix substrate. The latter option is advantageous in that the TFT active matrix substrate can be saved in the event that the resin base is not properly coated with GOS.

Each of the sensors 606 includes an upper electrode 612, a lower electrode 614, and a photoelectric transducer film 616 disposed between the upper electrode 612 and the lower electrode 614.

Since the upper electrode 612 is required to apply light emitted from the scintillator 608 to the photoelectric transducer film 616, the upper electrode 612 preferably is made of an electrically conductive material, which is transparent to at least the wavelength range of light emitted from the scintillator 608. More specifically, the upper electrode 612 preferably is made of transparent conducting oxide (TCO), which has a high transmittance to visible light and a low resistance value. Although the upper electrode 612 may be made of a thin film of metal such as gold or the like, the upper electrode 612 preferably is made of TCO, because the resistance value of gold is likely to increase if the transmittance is increased to 90% or higher. Examples of TCO include ITO, IZO, AZO, FTO, $SnO_2$, $TiO_2$, $ZnO_2$, etc., of which ITO is most preferable from the standpoint of process simplicity, low resistance, and transparency. The upper electrode 612 may be a single electrode, which is shared by all of the pixels, or may be a plurality of separate electrodes belonging to each of the respective pixels.

The photoelectric transducer film 616, which contains an organic photoconductor (OPC), absorbs light emitted from the scintillator 708, and generates electric charges depending on the absorbed light. The photoelectric transducer film 616, which contains an organic photoconductor (organic photoelectric transducer material), exhibits a sharp absorption spectrum in the visible wavelength range, and does not absorb electromagnetic waves other than light emitted from the scintillator 708. The sensors 606 are thus capable of effectively reducing noise, which would otherwise be generated if radiation 12 were absorbed by the photoelectric transducer film 616. The photoelectric transducer film 616 may contain amorphous silicon rather than an organic photoconductor. A photoelectric transducer film 616 that contains amorphous silicon exhibits a wide absorption spectrum for efficiently absorbing light emitted from the scintillator 708.

The organic photoconductor contained in the photoelectric transducer film 616 preferably has a peak wavelength for absorbing light, which is close to the peak wavelength of light emitted from the scintillator 708, in order to absorb the light emitted from the scintillator 708 most efficiently. The peak wavelength of light absorbed by the organic photoconductor should ideally be the same as the peak wavelength of light emitted from the scintillator 708. However, if the difference between such wavelengths is small enough, then the organic photoconductor can sufficiently absorb light emitted from the scintillator 708. More specifically, the difference between the peak wavelength of light absorbed by the organic photoconductor and the peak wavelength of light emitted from the scintillator 708 preferably is 10 nm or smaller, and more preferably, is 5 nm or smaller.

Examples of organic photoconductors that meet the above requirements include quinacridone-based organic compounds and phthalocyanine-based organic compounds. Inasmuch as the peak wavelength of light in the visible wavelength range, which is absorbed by quinacridone, is 560 nm, the organic photoconductor may be made of quinacridone and the scintillator 608 may be made of CsI(Tl), for thereby making it possible to reduce the difference between the peak wavelengths to 5 nm or smaller, and for substantially maximizing the amount of electric charges generated by the photoelectric transducer film 616.

Each of the sensors 606 includes an organic layer formed by superposing or mixing a region for absorbing electromagnetic waves, a photoelectric transducer region, an electron transport region, a hole transport region, an electron blocking region, a hole blocking region, a crystallization preventing region, electrodes, and an interlayer contact-improving region. The organic layer preferably contains an organic p-type compound (organic p-type semiconductor) or an organic n-type compound (organic n-type semiconductor).

The organic p-type semiconductor is a donor organic semiconductor (compound), mainly typified by a hole transport organic compound, and refers to an organic compound that tends to donate electrons. More specifically, in a case where two organic materials are used in contact with each other, one of the organic materials, which has a lower ionization potential, is referred to as a donor organic compound. Any of various organic compounds, which are capable of donating electrons, can be used as a donor organic compound.

The organic n-type semiconductor is an acceptor organic semiconductor (compound), mainly typified by an electron transport organic compound, and refers to an organic compound that tends to accept electrons. More specifically, in a case where two organic materials are used in contact with each other, one of the organic materials, which has a larger electron affinity, is referred to as an acceptor organic compound. Any of various organic compounds, which are capable of accepting electrons, can be used as an acceptor organic compound.

Materials, which can be used as the organic p-type semiconductor and the organic n-type semiconductor, and arrangements of the photoelectric transducer film 616 are disclosed in detail in Japanese Laid-Open Patent Publication No. 2009-032854, and will not be described in detail below. The photoelectric transducer film 616 may contain fullerene or carbon nanotubes.

The thickness of the photoelectric transducer film 616 should preferably be as large as possible, for thereby absorbing light from the scintillator 608. If the thickness of the photoelectric transducer film 616 is greater than a certain value, then the electric field intensity generated on the photoelectric transducer film 616 by the bias voltage applied from both ends of the photoelectric transducer film 616 is reduced, so that the photoelectric transducer film 616 cannot collect electric charges. The thickness of the photoelectric transducer film 616 preferably is in the range from 30 nm to 300 nm, more preferably, is in the range from 50 nm to 250 nm, and even more preferably, is in the range from 80 nm to 200 nm.

The photoelectric transducer film 616 comprises a single photoelectric transducer film, which is shared by all of the pixels, however, the photoelectric transducer film 616 may also comprise a plurality of separate photoelectric transducer films belonging respectively to each of the pixels. The lower electrode 614 comprises a plurality of separate lower electrodes belonging to the respective pixels, however, the lower electrode may also comprise a single lower electrode, which is shared by all of the pixels. The lower electrode 614 may be made of an electrically conductive material, which is transparent or opaque, and preferably is made of aluminum, silver, or the like. The lower electrode 614 has a thickness in the range from 30 nm to 300 nm, for example.

In each of the sensors 606, a prescribed bias voltage is applied between the upper electrode 612 and the lower electrode 614, so as to move one type of electric charges, i.e., either electrons or holes, generated by the photoelectric transducer film 616 to the upper electrode 612, and to move the other type of electric charges to the lower electrode 614. In the modified radiation detector 600, the bias voltage is applied to the upper electrode 612 through a wire connected thereto. The bias voltage has a polarity such that electrons generated by the photoelectric transducer film 616 move to the upper electrode 612, and holes move to the lower electrode 614. However, the bias voltage may be of an opposite polarity.

The sensor 606 of each of the pixels may include at least the lower electrode 614, the photoelectric transducer film 616, and the upper electrode 612. In order to prevent an increase in dark current, the sensor 606 preferably includes in addition at least one of an electron blocking film 618 and a hole blocking film 620, and more preferably, includes both of such films.

The electron blocking film 618 may be disposed between the lower electrode 614 and the photoelectric transducer film 616. The electron blocking film 618 is effective to prevent an increase in dark current, due to electrons being introduced from the lower electrode 614 into the photoelectric transducer film 616 in a case where the bias voltage is applied between the lower electrode 614 and the upper electrode 612.

The electron blocking film 618 may be made of an electron-donating organic material. Actually, the material of the electron blocking film 618 may be selected depending on the material of the adjacent lower electrode 614 and the material of the adjacent photoelectric transducer film 616. The material of the electron blocking film 618 preferably has an electron affinity (Ea), which is greater than the work function (Wf) of the material of the adjacent lower electrode 614 by 1.3 eV or higher, and preferably also has an ionization potential (Ip), which is equal to or smaller than the ionization potential of the material of the adjacent photoelectric transducer film 616. Materials applicable as the electron-releasing organic material are described in detail in Japanese Laid-Open Patent Publication No. 2009-032854, and will not be described below.

The electron blocking film 618 has a thickness preferably in the range from 10 nm to 200 nm, more preferably, in the range from 30 nm to 150 nm, and even more preferably, in the range from 50 nm to 100 nm, in order to provide a reliable dark current preventing effect, and also to prevent the photoelectric transducing efficiency of the sensor 606 from being reduced.

The hole blocking film 620 is disposed between the photoelectric transducer film 616 and the upper electrode 612. The hole blocking film 620 is effective to prevent an increase in dark current, due to electrons being introduced from the upper electrode 612 into the photoelectric transducer film 616 in a case where the bias voltage is applied between the lower electrode 614 and the upper electrode 612.

The hole blocking film 620 may be made of an electron-accepting organic material. The hole blocking film 620 has a thickness preferably in the range from 10 nm to 200 nm, more preferably, in the range from 30 nm to 150 nm, and even more preferably, in the range from 50 nm to 100 nm, in order to provide a reliable dark current preventing effect, and also to prevent the photoelectric transducing efficiency of the sensor 606 from being reduced.

Actually, the material of the hole blocking film 620 may be selected depending on the material of the adjacent upper electrode 612 and the material of the adjacent photoelectric transducer film 616. The material of the hole blocking film 620 preferably has an ionization potential (Ip), which is equal to or greater than the work function (Wf) of the material of the adjacent upper electrode 612 by 1.3 eV or higher, and preferably also has an electron affinity (Ea), which is equal to or greater than the electron affinity of the material of the adjacent photoelectric transducer film 616. Materials applicable as the electron-accepting organic material are described in detail in Japanese Laid-Open Patent Publication No. 2009-032854, and will not be described below.

For setting the bias voltage in order to cause holes generated in the photoelectric transducer film 616 to move to the upper electrode 612, and also to cause electrons generated in the photoelectric transducer film 616 to move to the lower electrode 614, the electron blocking film 618 and the hole blocking film 620 may be switched in position. It is not necessary for the modified radiation detector 600 to have both the electron blocking film 618 and the hole blocking film 620, but either one of such films may be included, to thereby provide a certain reliable dark current preventing effect.

As shown in FIG. 10, the signal output units 604 are disposed on the surface of the substrate 602 in alignment respectively with the lower electrodes 614 of the pixels. Each of the signal output units 604 has a storage capacitor 622 for storing electric charges moved to the lower electrode 614, and a TFT 624 for converting electric charges stored in the storage capacitor 622 into electric signals and outputting the electric signals. The storage capacitor 622 and the TFT 624 are disposed in an area underlapping the lower electrode 614 as viewed in plan, so that the signal output unit 604 and the sensor 606 of each pixel are superposed in the thickness direction of the modified radiation detector 600. In the signal output unit 604, the lower electrode 614 fully covers the storage capacitor 622, and the TFT 624 minimizes the surface area of the modified radiation detector 600 including the pixels thereof.

Each of the storage capacitors 622 is connected to a corresponding lower electrode 614 by an interconnecting structure, which is made of an electrically conductive material that extends through an insulating film 626 disposed between the substrate 602 and the lower electrode 614. Electric charges that are collected by the lower electrode 614 can be moved to the storage capacitor 622 via the interconnecting structure.

As shown in FIG. 11, each of the TFTs 624 includes a gate electrode 628, a gate insulating film 630, and an active layer (channel layer) 632, which are stacked together, and a source electrode 634 and a drain electrode 636 disposed on the active layer 632 and which are spaced from each other. The active layer 632 may be made of amorphous silicon, an amorphous oxide, an organic semiconductor material, carbon nanotubes, or the like. However, the material of the active layer 632 is not limited to such materials.

The amorphous oxide, which may be used for forming the active layer 632, preferably is an oxide, e.g., an In—O oxide containing at least one of In, Ga, and Zn, more preferably is an oxide, e.g., an In—Zn—O oxide, an In—Ga—O oxide, or a Ga—Zn—O oxide containing at least two of In, Ga, and Zn, or even more preferably, is an oxide containing In, Ga, and Zn. The In—Ga-An-O amorphous oxide preferably is an amorphous oxide having a crystalline state represented by $InGaO_3(ZnO)_m$ (where m is a natural number smaller than 6), or more preferably, $InGaZnO_4$. However, the amorphous oxide of the active layer 632 is not limited to the above materials.

The organic semiconductor material, which the active layer 632 may be made of, may be, but should not be limited to, a phthalocyanine compound, pentacene, vanadylphthalocyanine, or the like. Details of a phthalocyanine compound are described in Japanese Laid-Open Patent Publication No. 2009-212389, and will not be described below.

The active layer 632 of the TFT 624, which is made of amorphous oxide, an organic semiconductor material, or carbon nanotubes, does not absorb radiation 12 such as X-rays or the like, or only absorbs trace amounts of such radiation 12, thereby effectively preventing the signal output unit 604 from producing noise.

If the active layer 632 is made of carbon nanotubes, then the switching speed of the TFT 624 is increased, and the TFT 624 has a low light absorption level in the visible wavelength range. If the active layer 632 is fabricated of carbon nanotubes, and if even an extremely small amount of metal impurity is introduced into the active layer 632, the capability of the TFT 624 is greatly lowered. Therefore, it is necessary to separate and extract highly pure carbon nanotubes by way of centrifugal separation or the like.

The amorphous oxide, the organic semiconductor material, the carbon nanotubes, and the organic photoconductor referred to above can be grown as a film at low temperatures. Therefore, the substrate 602 is not limited to a heat-resistant substrate, such as a semiconductor substrate, a quartz substrate, or a glass substrate, but may be a flexible substrate of plastic or a substrate made of aramid or bionanofibers. More specifically, the substrate 602 may be a flexible substrate of polyester, such as polyethylene terephthalate, polybutylene phthalate, polyethylene naphthalate, or the like, or polystyrene, polycarbonate, polyethersulfone, polyarylate, polyimide, polycycloolefine, norbornene resin, polychlorotrifluoroethylene, or the like. Such a flexible substrate of plastic makes the modified radiation detector 600 lighter in weight and hence easier to carry.

The photoelectric transducer film 616 may be made of an organic photoconductor, and the TFT 624 may be made of an organic semiconductor material, which can be grown on a flexible plastic substrate, i.e., the substrate 602, at low temperatures, whereby the modified radiation detector 600 can be reduced in thickness and weight as a whole. The radiation detecting apparatus 20, which incorporates the radiation detector 600 therein, can also be reduced in thickness and weight, thereby making the radiation detecting apparatus 20 convenient for use outside of a hospital or the like. Since the substrate 602, which serves as a base member for the photoelectric transducer, is made of a flexible material rather than glass, the radiation detector 600 is resistant to damage when the radiation detecting apparatus 20 is carried.

The substrate 602 may include an insulative layer for making the substrate 602 insulative, a gas barrier layer for making the substrate 602 impermeable to water and oxygen, and an undercoat layer for increasing the flatness of the substrate 602, thereby making the substrate 602 capable of closely contacting electrodes.

Aramid is advantageous in that, since a high-temperature process at 200 degrees Celsius is applicable thereto, aramid allows a transparent electrode material to be set at a high temperature for achieving lower resistance. Aramid also allows driver ICs to be automatically mounted thereon by a process including a solder reflow process. Furthermore, inasmuch as aramid has a coefficient of thermal expansion close to that of ITO (Indium Tin Oxide) and glass, a substrate 602 made of aramid is less liable to become warped or cracked after fabrication. In addition, a substrate 602 of aramid may be made thinner than a glass substrate or the like. The substrate 602 may be in the form of a stacked assembly of an ultrathin glass substrate and an aramid film.

Bionanofibers are made by compounding a bundle of cellulose microfibrils (bacteria cellulose) produced by bacteria (acetic acid bacteria, *Acetobacter Xylinum*) and a transparent resin. The bundle of cellulose microfibrils has a width of 50 nm, which is 1/10 of the wavelength of visible light, is highly strong and highly resilient, and is subject to low thermal expansion. Bionanofibers, which contain 60% to 70% of fibers and exhibit a light transmittance of approximately 90% at a wavelength of 500 nm, can be produced by impregnating bacteria cellulose with a transparent resin such as an acrylic resin, an epoxy resin, or the like, and then setting the transparent resin. Bionanofibers are flexible, and have a low coefficient of thermal expansion ranging from 3 ppm to 7 ppm, which is comparable to silicon crystals, a high strength of 460 MPa that matches the strength of steel, and a high resiliency of 30 GPa. Therefore, a substrate 602 made of bionanofibers can be thinner than glass substrates or the like.

According to the present modification, the signal output units 604, the sensors 606, and the transparent insulating film 610 are successively disposed on the substrate 602, and the scintillator 608 is bonded to the transparent insulating film 610 by an adhesive resin of low light absorption, thereby producing the radiation detector 600.

Since the photoelectric transducer film 616 is made of an organic photoconductor, and the active layer 632 of each TFT 624 is made of an organic semiconductor material, the photoelectric transducer film 616 and the signal output units 604 essentially do not absorb radiation 12. Consequently, the sensitivity of the modified radiation detector 600 is prevented from being lowered.

The organic semiconductor material of the active layer 632 of each TFT 624, and the organic photoconductor of the photoelectric transducer film 616 can be grown as a film at low temperatures. Therefore, the substrate 602 may be made of plastics, aramid, or bionanofibers, in order to further prevent the sensitivity of the modified radiation detector 600 from being lowered.

If the modified radiation detector 600 is bonded to the irradiated surface 32 in the casing, and the substrate 602 is made of highly rigid plastics, aramid, or bionanofibers, then since the rigidity of the radiation detector 600 is increased, the portion of the casing around the irradiated surface 32 can be made thin. If the substrate 602 is made of highly rigid plastics, aramid, or bionanofibers, then since the radiation detector 600 is flexible, the radiation detector 600 is less liable to be damaged in a case where shocks are applied to the irradiated surface 32.

The modified radiation detector 600 is of a PSS (Penetration Side Sampling) type as a reverse-side readout type, wherein the sensors 606 (the photoelectric transducer film 616), which are positioned behind the scintillator 608 remotely from the radiation source 16, convert light emitted from the scintillator 608 into electric charges in order to read radiographic image information. However, the modified radiation detector 600 is not limited to a PSS type.

The modified radiation detector 600 may be a face-side readout ISS (Irradiation Side Sampling) type of radiation detector, in which the substrate 602, the signal output units 604, the sensors 606, and the scintillator 608 are arranged successively along the direction in which radiation 12 is applied, and the sensors 606, which are positioned in front of the scintillator 608 proximate the radiation source 16, convert light emitted from the scintillator 608 into electric charges in order to read radiographic image information. In accordance with such an ISS type radiation detector, inasmuch as light emitted from the scintillator 608 is prevented from being scattered and attenuated before the light is detected by the sensors 606, the generated radiographic image information is of high resolution.

Although certain preferred embodiments of the present invention have been shown and described in detail, it should be understood that various changes and modifications may be made to the embodiments without departing from the scope of the invention as set forth in the appended claims.

What is claimed is:

1. A radiation detecting apparatus comprising:
    a radiation detector including
        a scintillator configured to convert radiation that has passed through a subject into visible light, and
        a substantially rectangular shaped photoelectric transducer board configured to convert the visible light into radiographic image information; and
    a casing housing the radiation detector therein,
    wherein the casing is of a substantially rectangular shape and includes an upper plate, a lower plate, and a side plate interconnecting the upper plate and the lower plate;
    the side plate has a recess defined therein, which faces and is spaced from a corner of the photoelectric transducer board, the recess being concave in a direction away from the corner;
    the corner of the photoelectric transducer board has a chamfer in an area that faces the recess;
    the recess comprises a cavity, which is concave as viewed in plan;
    the cavity includes
        two side wall surfaces configured to adjoin the respective inner wall surfaces, and
        a bottom surface configured to interconnect the two side wall surfaces;
    the chamfer of the corner of the photoelectric transducer board includes two apexes as viewed in plan; and
    a space is present between the chamfer and the bottom surface of the cavity, the chamfer and the bottom surface of the cavity facing each other and substantially parallel to each other.

2. The radiation detecting apparatus according to claim 1, wherein one of the two apexes that is closest to the bottom surface is spaced from the bottom surface of the cavity by a minimum distance of a range from 1 mm to 5 mm.

3. The radiation detecting apparatus according to claim 2, wherein the recess comprises a cavity, which is concave as viewed in plan, and which is concave as viewed in vertical cross section;
    the cavity is defined between a first surface, which is closer to the upper plate, and a second surface, which is closer to the lower plate;
    the photoelectric transducer board has a surface facing the upper plate and spaced from the first surface by a minimum distance, and a surface facing the lower plate and spaced from the second surface by a minimum distance, each of the minimum distances being in the range from 1 mm to 5 mm.

4. The radiation detecting apparatus according to claim 3, further comprising:
    a first base plate disposed between the upper plate and the photoelectric transducer board and supporting the radiation detector thereon;
    the scintillator is disposed on a surface of the photoelectric transducer board, which is remote from the first base plate; and
    the first base plate has a thickness ta, the photoelectric transducer board has a thickness tb, the scintillator has a thickness tc, and the cavity has a height ha along a thickness direction of the photoelectric transducer board, the thicknesses ta, tb, tc and the height ha being related to each other by the inequality tb <ha <(ta +tb +tc).

5. The radiation detecting apparatus according to claim 4, wherein the photoelectric transducer board has a transverse length greater than a transverse length of the scintillator, and a longitudinal length greater than a longitudinal length of the scintillator.

6. The radiation detecting apparatus according to claim 4, wherein the upper plate and the first base plate are fixed to each other by an adhesive layer; and
    the first base plate and the photoelectric transducer board are bonded to each other by a pressure-sensitive adhesive.

7. The radiation detecting apparatus according to claim 4, further comprising:
    a second base plate disposed between the scintillator and the lower plate, and which supports the radiation detector thereon in coaction with the first base plate;
    the upper plate and the first base plate are fixed to each other by an adhesive layer;
    the first base plate and the photoelectric transducer board are bonded to each other by a pressure-sensitive adhesive; and
    the second base plate and the scintillator are bonded to each other by a pressure-sensitive adhesive.

8. The radiation detecting apparatus according to claim 7, wherein the first base plate is made of a non-metal material; and
    the second base plate is made principally of a non-metal material.

* * * * *